US012693438B2

(12) United States Patent
Urushiyama et al.

(10) Patent No.: US 12,693,438 B2
(45) Date of Patent: Jul. 28, 2026

(54) RADIATION IMAGE IMAGING APPARATUS

(71) Applicant: KONICA MINOLTA, INC., Tokyo (JP)

(72) Inventors: Sho Urushiyama, Kiyose (JP); Keisuke Koeda, Tokorozawa (JP)

(73) Assignee: KONICA MINOLTA, INC., Tokyo (JP)

( * ) Notice: Subject to any disclaimer, the term of this patent is extended or adjusted under 35 U.S.C. 154(b) by 216 days.

(21) Appl. No.: 18/768,529

(22) Filed: Jul. 10, 2024

(65) Prior Publication Data

US 2025/0020819 A1 Jan. 16, 2025

(30) Foreign Application Priority Data

Jul. 13, 2023 (JP) ................................. 2023-115101

(51) Int. Cl.
| | |
|---|---|
| *G01T 1/24* | (2006.01) |
| *A61B 6/00* | (2006.01) |
| *A61B 6/42* | (2024.01) |
| *G01T 7/00* | (2006.01) |

(52) U.S. Cl.
CPC ................ *G01T 1/247* (2013.01); *A61B 6/42* (2013.01); *A61B 6/4488* (2013.01); *A61B 6/485* (2013.01); *G01T 7/00* (2013.01)

(58) Field of Classification Search
None
See application file for complete search history.

(56) References Cited

U.S. PATENT DOCUMENTS

| | | | | |
|---|---|---|---|---|
| 7,866,163 | B2 * | 1/2011 | Ertel | ..................... G01T 1/2928 |
| | | | | 62/3.2 |
| 12,047,677 | B2 * | 7/2024 | Kida | ........................ A61B 6/00 |

FOREIGN PATENT DOCUMENTS

JP 2013176563 A 9/2013

* cited by examiner

*Primary Examiner* — Marcus H Taningco
(74) *Attorney, Agent, or Firm* — BUCHANAN INGERSOLL & ROONEY PC

(57) ABSTRACT

Disclosed is a radiation image imaging apparatus including: a radiation detector that detects radiation; a hardware processor that controls imaging of a radiation image by driving a readout circuit in a first power consumption mode or a second power consumption mode in which power consumption is larger than in the first power consumption mode; and a housing that houses the radiation detector and the hardware processor. The hardware processor enables imaging in the second power consumption mode in response to the radiation image imaging apparatus being in contact with a heat suppressor and prohibits the imaging in the second power consumption mode or stops driving of the readout circuit in the second power consumption mode after end of the imaging in the second power consumption mode in response to the radiation image imaging apparatus being not in contact with the heat suppressor.

5 Claims, 4 Drawing Sheets

RADIATION IMAGE IMAGING APPARATUS

BACKGROUND OF THE INVENTION

Technical Field

The present invention relates to a radiation image imaging apparatus.

Description of Related Art

Conventionally, some readout circuits (ROIC) of a radiation image imaging apparatus such as a flat panel detector (FPD) can operate while switching between a plurality of different power consumption modes. In such a radiation image imaging apparatus, as the readout circuit operates in a mode with higher power consumption, the slew rate increases, and a low-noise image can be generated even at the same frame rate.

However, in a case where the readout circuit is operating in the high power consumption mode, a large amount of heat is generated, and thus a technician or the like may directly touch the radiation image imaging apparatus in a high-temperature state and be injured. For example, it is conceivable that a burn may be inflicted when the radiation image imaging apparatus is removed from the imaging table, or that the radiation image imaging apparatus may be dropped and broken.

In this case, Japanese Unexamined Patent Publication No. 2013-176563 discloses that when the radiation detection sensor is in contact with the cooling mechanism, control of moving image imaging is performed, and when the radiation detection sensor is not in contact with the cooling mechanism, processing for limiting the imaging frame rate of the radiation detection sensor is executed.

SUMMARY OF THE INVENTION

However, the radiation-detecting sensor described in Japanese Unexamined Patent Publication No. 2013-176563 does not have a readout circuit that can operate by switching between a plurality of different power consumption modes.

The power consumption of the readout circuit capable of switching a plurality of different power consumption modes does not depend on the frame rate, but depends on the power consumption mode set in the readout circuit. Therefore, in a case where the radiation detection sensor is not in contact with the cooling mechanism, even if the frame rate is limited, the temperature becomes high in a case where the readout circuit is driven in the high power consumption mode, and thus it is not possible to safely use the radiation detection sensor.

An object of the present invention is to enable safe use of a high power consumption mode in a radiation image imaging apparatus including a readout circuit that can operate while switching between a plurality of different power consumption modes.

To achieve at least one of the abovementioned objects, according to an aspect of the present invention, radiation image imaging apparatus reflecting one aspect of the present invention includes: a radiation detector that detects radiation; a hardware processor that controls imaging of a radiation image by driving a readout circuit that reads out an image signal from the radiation detector in a first power consumption mode or a second power consumption mode in which power consumption is larger than power consumption in the first power consumption mode; and a housing that houses the radiation detector and the hardware processor, wherein the hardware processor enables imaging in the second power consumption mode in response to the radiation image imaging apparatus being in contact with a heat suppressor that suppresses an increase in a surface temperature of the housing, and prohibits the imaging in the second power consumption mode or stops driving of the readout circuit in the second power consumption mode after end of the imaging in the second power consumption mode in response to the radiation image imaging apparatus being not in contact with the heat suppressor.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION

Hereinafter, one or more embodiments of the present invention will be described with reference to the drawings. However, the scope of the invention is not limited to the disclosed embodiments.

First Embodiment

First, a first embodiment of the present invention will be described.

[Configuration of FPD1]

First, the configuration of a FPD1 in an embodiment of the present invention will be described.

The FPD1 is a portable radiation image imaging apparatus. The FPD1 is used by being mounted on an imaging table (not illustrated) in an imaging room in a medical facility or by being arranged on a bed in a hospital room or an operation room. The FPD1 is irradiated with radiations from a radiation source (not illustrated), generates charges corresponding to the radiations transmitted through a subject, and reads the generated charges as image data.

Figure 1:
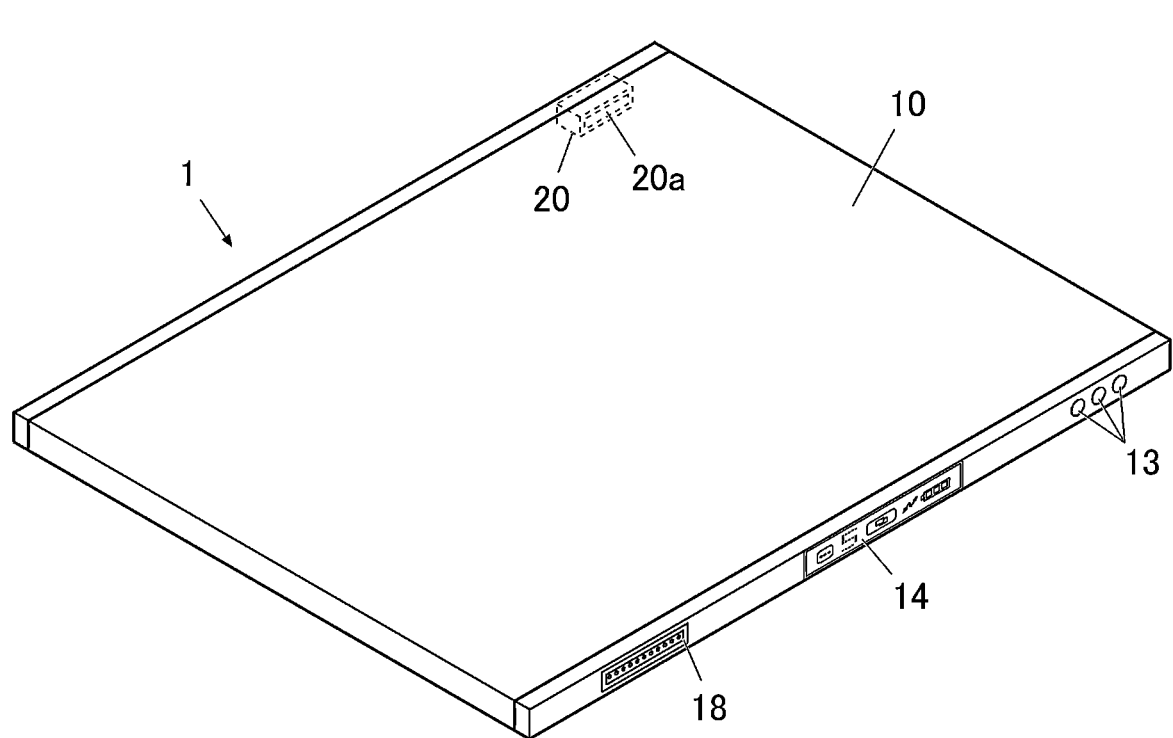
FIG. 1 is a diagram illustrating an example of an external configuration of a radiation image imaging apparatus.
Figure 2:
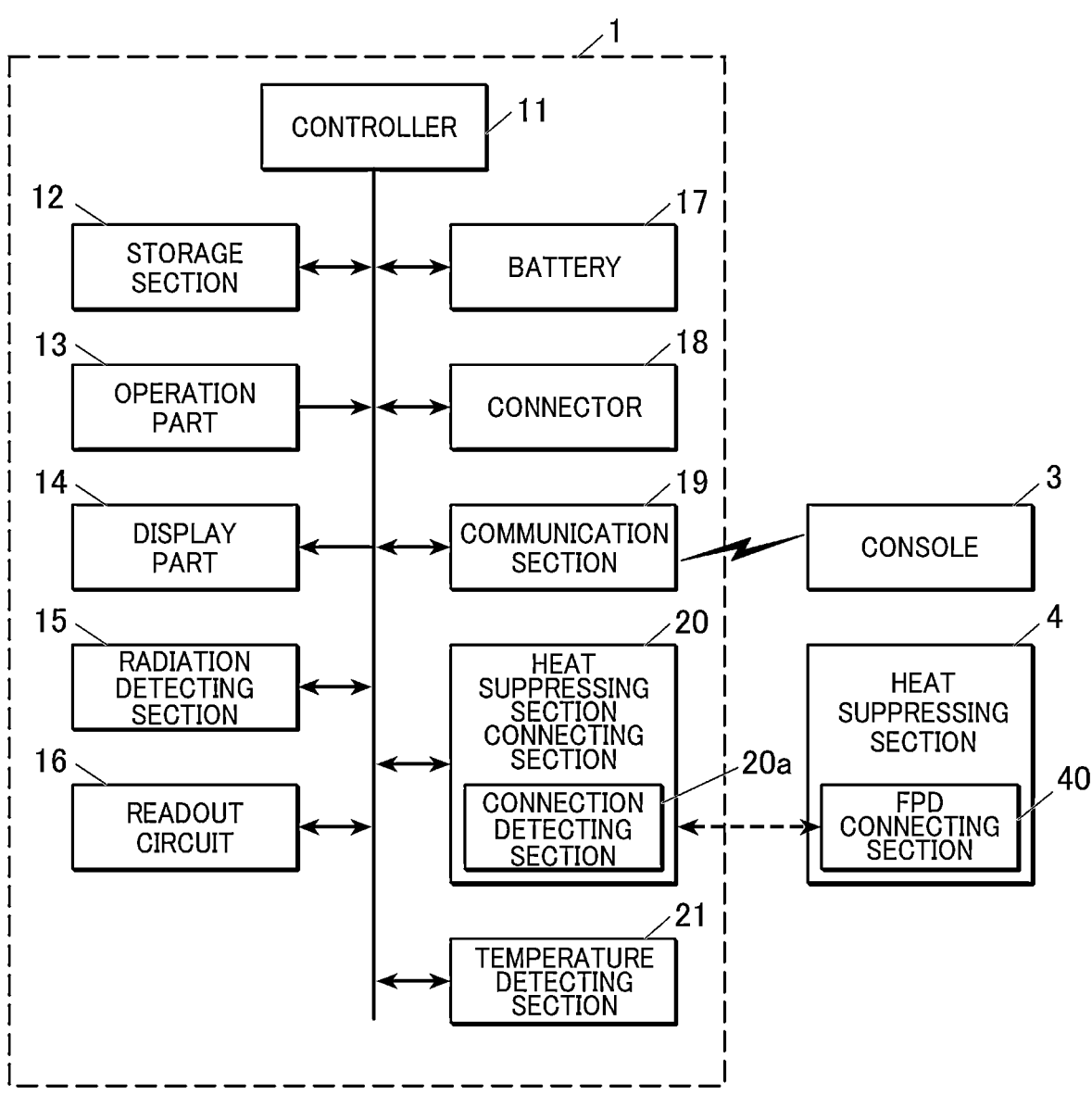
FIG. 2 is a block diagram illustrating a functional configuration of the radiation image imaging apparatus.

FIG. 1 is a perspective view illustrating an example of an appearance configuration of a FPD1. FIG. 2 is a block diagram illustrating the functional configuration of a FPD1.

As illustrated in FIGS. 1 and 2, the FPD1 is configured to include a controller 11 (hardware processor), a storage section 12, an operation part 13, a display part 14, a radiation detecting section 15 (radiation detector), a readout circuit 16, a battery 17, a connector 18, a communication section 19, a heat suppressing section connecting section 20, a temperature detecting section 21 (temperature detector), and the like.

The controller 11 is constituted by a central processing unit (CPU), a random access memory (RAM), and the like. The controller 11 reads various programs stored in the storage section 12, develops the programs in the RAM, and centrally controls each unit of the FPD1 in accordance with the developed programs. Note that the controller 11 may be formed with a field programmable gate array (FPGA) or the like.

The storage section 12 is formed with a nonvolatile semiconductor memory or the like. The storage section 12 stores various programs executed by the controller 11, parameters necessary for execution of processing by the programs, or data such as processing results.

The operation part 13 includes a power switch, a switch for switching to a standby state, and the like. The operation part 13 outputs operation signals of various switches by a user to the controller 11.

Under the control of the controller 11, the display part 14 displays various types of information. For example, as illustrated in FIG. 1, the display part 14 is provided on a side surface of the housing 10 of the FPD1.

The radiation detecting section 15 includes, for example, radiation detection elements two dimensionally arranged on a glass substrate. The radiation detection elements are formed by semiconductor image sensors, such as photo-diodes. The radiation detection elements accumulate charge corresponding to the dose of radiation that has been applied from a radiation source (not illustrated) and has passed through at least a subject. Each radiation detection element is connected to a switching section such as a thin film transistor (TFT), for example, and the switching section controls accumulation of charges in the radiation detection element and discharge of charges from the radiation detection element to the signal line. Note that the radiation detecting section 15 may be of an indirect conversion type in which radiation is converted into electrical signals by photoelectric conversion elements via a scintillator, or a direct conversion type in which radiation is directly converted into electrical signals, and either type may be used.

The readout circuit (ROIC) 16 includes an integration circuit, a correlated double sampling circuit, an analog multiplexer, an A/D converter, and the like. The readout circuit 16 collects and accumulates charges emitted from each radiation detection element of the radiation detecting section 15 to a signal line, converts the accumulated charge amount into an image signal (image data), and reads out the image signal.

The readout circuit 16 is driven in either the first power consumption mode or the second power consumption mode during imaging. In the second power consumption mode, the power consumption is larger than that in the first power consumption mode, that is, the amount of heat generation is larger. The readout circuit 16 has a higher slew rate when driven in the second power consumption mode than when driven in the first power consumption mode and can gener-ate a low-noise image when imaging is performed at the same frame rate.

The battery 17 accumulates (charges) power supplied from an external device such as a cradle, a medical cart, or an imaging table (not shown) connected via the connector 18 and supplies the power to each unit of the FPD1.

The connector 18 is a connection section that can be electrically connected to an external device by being con-nected to a connector of the external device (not shown) directly or via a cable.

The communication section 19 transmits and receives data to and from the console 3 or the like in a wireless manner or a wired manner via an antenna (not shown) or the connector 18.

Here, the console 3 is a computer including a controller, a storage section, an operation part, a display part, and a communication section (not illustrated). The console 3 receives an operation such as selection of an imaging condition including an imaging mode and start/end of imag-ing by the user. The console 3 transmits information on imaging conditions including an imaging mode and an imaging start/end instruction to a radiation source and a FPD1 (not illustrated) in response to a user operation to control imaging. Further, the console 3 displays a notifica-tion, a warning, and the like transmitted from the FPD1.

Here, the imaging modes for FPD1 include a serial imaging mode, a fluoroscopy mode, and a still-image imag-ing mode.

Both serial imaging and fluoroscopy are moving image imaging for imaging a moving image including a plurality of frames, but the obtained image quality and the imaging time are different. Fluoroscopy is performed, for example, during surgery and requires imaging for a longer time than general serial imaging. For example, serial imaging is imaging for about 30 seconds, but fluoroscopy may continue imaging for one hour if it is long. The controller 11 of the FPD1 performs imaging by driving the readout circuit 16 in the first power consumption mode in serial imaging. Since imaging for a long time such as fluoroscopy and surgery is required, it is necessary to suppress the dose per unit time, and a low-noise image is required. Therefore, the controller 11 drives the readout circuit 16 in the second power consumption mode in fluoroscopy to perform imaging.

A serial imaging mode in which serial imaging is per-formed in a FPD1 is referred to as a first moving image imaging mode. A fluoroscopy mode in which fluoroscopy is performed in a FPD1 is referred to as a second moving image imaging mode. In the first moving image imaging mode and the second moving image imaging mode, imaging at the same frame rate is possible. The controller 11 drives the readout circuit 16 in the first power consumption mode in the first moving image imaging mode and drives the readout circuit 16 in the second power consumption mode in the second moving image imaging mode.

The heat suppressing section connecting section 20 is a connecting section to the heat suppressing section 4 (heat suppressor).

The heat suppressing section 4 is a device or a member that suppresses an increase in surface temperature of the housing 10 on the FPD1. Examples of the heat suppressing section 4 include an air cooling mechanism, a water cooling mechanism, a heat storage material, and a heat transfer material. Examples of the air cooling mechanism include an air cooling fan. Examples of the water cooling mechanism include a water cooling fan. The heat storage material includes, for example, a latent heat storage material (PCM). Examples of the heat transfer material include a heat-conducting silicone sheet and a heat-conducting tape. The heat suppressing section 4 is attached to an imaging table or a bed. The heat suppressing section 4 may be externally attached to the FPD1.

The heat suppressing section connecting section 20 includes a connection detecting section 20a for detecting the connection with the heat suppressing section 4. For example, the heat suppressing section connecting section 20 is con-nected to (e.g., engaged with) the FPD connecting section 40 of the heat suppressing section 4 when the heat suppressing section connecting section 20 is mounted on an imaging table or a bed to which the heat suppressing section 4 is attached in a manner such that a FPD1 portion of the imaging table or the bed is in contact with the heat sup-pressing section 4. Alternatively, the heat suppressing sec-tion connecting section 20 is configured to be connected to (e.g., engaged with) the FPD connecting section 40 provided in the external heat suppressing section 4 when the external heat suppressing section 4 is attached in a manner contacting the FPD1. The connection detecting section 20a detects connection to the FPD connecting section 40 and outputs a detection signal to the controller 11. The contact referred to herein includes not only physical (direct) contact but also indirect contact with a mechanism to release heat, such as a cooling fan or a water cooling fan. FIG. 1 illustrates a configuration in which the connection detecting section 20a and the connector 18 are provided, respectively, but a configuration may be adopted in which the connector 18 also serves as the connection detecting section 20a. In the case of such a configuration, there is an effect that the design of the FPD1 can be simplified, and the cost can be reduced.

Note that when the heat suppressing section 4 is a water cooling mechanism or a cooling mechanism, the heat suppressing section 4 includes a connection detector (not illustrated) that detects connection to the FPD1. When the connection with the FPD1 is detected by the connection detector, the heat suppressing section 4 starts the heat exhaust driving.

The temperature detecting section 21 detects the temperature of the housing 10 at the FPD1 and outputs the temperature to the controller 11. It is desirable to install the temperature detecting section 21 in the vicinity of the readout circuit 16 that generates a large amount of heat.

[Operation of FPD1]

Next, an operation in the first embodiment will be described.

When the power of the FPD1 is turned on, the controller 11 causes each unit to shift to a standby state. The standby state is a state of waiting for transmission of an imaging start instruction signal from the console 3. In the standby state, the controller 11 causes the readout circuit 16 to shift to the sleep mode or the first power consumption mode. The sleep mode is a mode in which power supply to the readout circuit 16 is reduced to such an extent that image acquisition cannot be performed. In the sleep mode, the power consumption is lower than that in the first power consumption mode, but it takes time to shift to a power consumption state in which imaging is possible. In the first power consumption mode, imaging can be performed without a shift time, but the power consumption is higher than that in the sleep mode. Whether the readout circuit 16 is set to the sleep mode or the first power consumption mode in the standby state is set in advance. This setting can be switched in response to, for example, an operation of a switch for switching to a standby state of the operation part 13.

Upon reception of the information on the imaging conditions including the imaging mode from the console 3 and the imaging start instruction signal by the communication section 19, the controller 11 executes the readout circuit control processing A.

Here, in the FPD1, imaging in the first power consumption mode and imaging in the second power consumption mode, and general imaging and mobile imaging are used in a mixed manner. The general imaging is imaging on an imaging table in an imaging room. That is, the FPD1 used for imaging is taken out and transported for the next imaging after the end of imaging. However, when imaging is performed by driving the readout circuit 16 in the second power consumption mode in a state in which the heat suppressing section 4 is not in contact, the temperature of the FPD1 of the housing 10 on the upper side becomes high. Therefore, there is a possibility that the user burns by directly touching the FPD1 or breaks a bone by dropping the FPD1.

Therefore, in the FPD1, the readout circuit control processing A is executed at the time of imaging to control the driving of the readout circuit 16 so that the FPD1 can be used safely.

Figure 3:
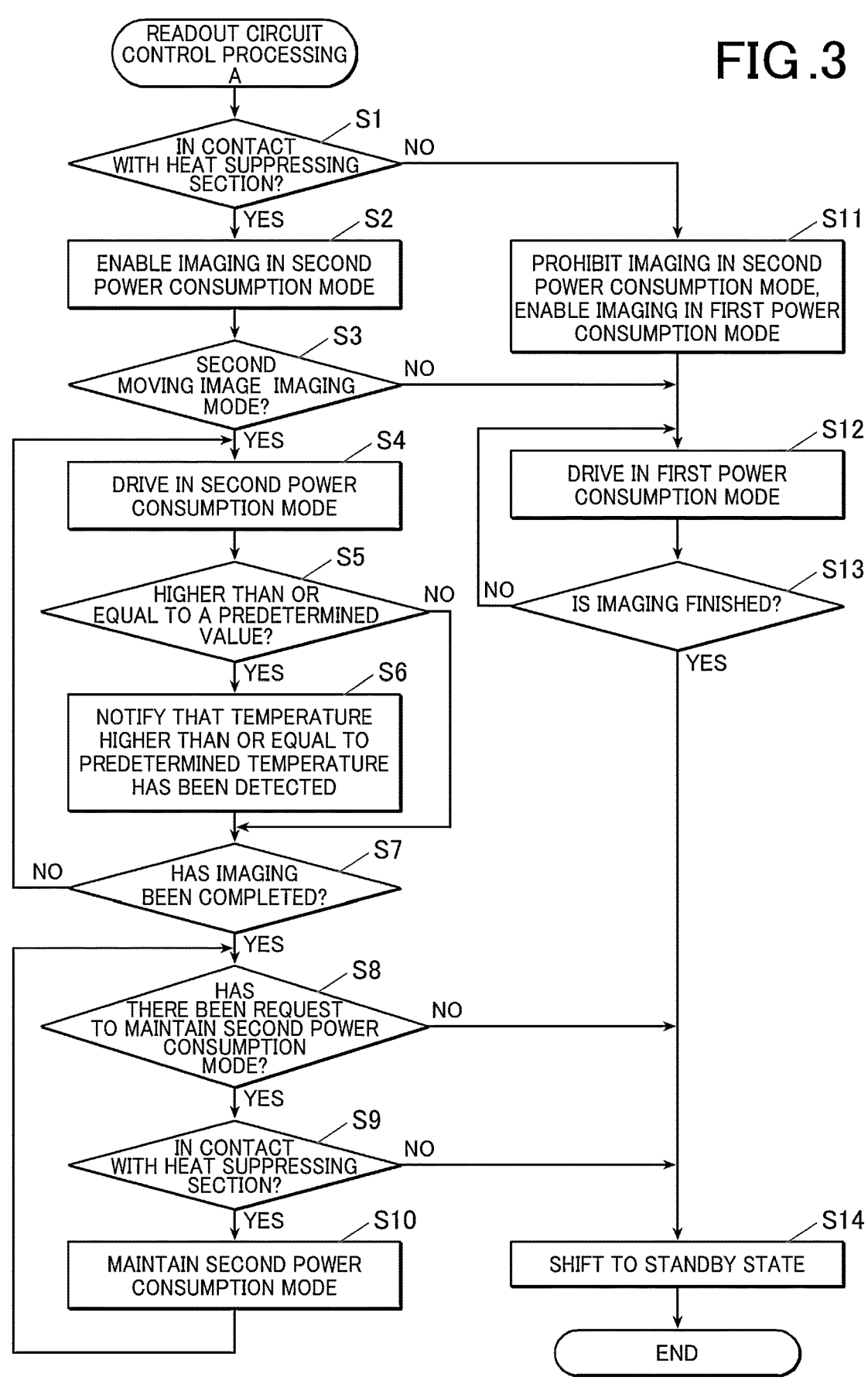
FIG. 3 is a flowchart illustrating a flow of readout circuit control processing A executed by a controller in FIG. 2.

FIG. 3 is a flowchart illustrating a flow of readout circuit control processing A. The readout circuit control processing A is executed by the controller 11 in cooperation with the program stored in the storage section 12.

In the readout circuit control processing A, first, the controller 11 determines whether or not the FPD1 is in contact with the heat suppressing section 4 (step S1).

The controller 11 determines, based on the signal input from the connection detecting section 20a, whether the FPD1 is in contact with the heat suppressing section 4.

If the controller 11 determines that the FPD1 is in contact with the heat suppressing section 4 (step S1; YES), the controller 11 enables imaging in the second power consumption mode (step S2).

That is, the controller 11 enables driving of the readout circuit 16 in the second power consumption mode.

Next, the controller 11 determines whether or not the imaging mode is the second moving image imaging mode (step S3).

The controller 11 determines whether or not the imaging mode is the second moving image imaging mode based on the information of the imaging mode transmitted from the console 3.

When it is determined that the imaging mode is not the second moving image imaging mode (Step S3; NO), the controller 11 proceeds to Step S12.

That is, when determining that the imaging mode is the first moving image imaging mode or the still-image imaging mode, the controller 11 proceeds to step S12.

If the controller 11 determines that the imaging mode is the second moving image imaging mode (YES in step S3), the controller 11 drives the readout circuit 16 in the second power consumption mode (step S4).

Next, the controller 11 refers to the temperature detecting section 21 and determines whether the temperature of the housing 10 at the FPD1 is higher than or equal to a predetermined value (step S5).

If the controller 11 determines that the temperature of the housing 10 at the FPD1 is not higher than or equal to the predetermined value (step S5; NO), the controller 11 proceeds to step S7.

If the controller 11 determines that the temperature of the housing 10 on the FPD1 is higher than or equal to the predetermined temperature (YES in step S5), the controller 11 provides notification (warning) that a temperature higher than or equal to the predetermined temperature has been detected in the housing 10 on the FPD1 (step S6). Then, the controller 11 proceeds to step S7.

In step S6, for example, the controller 11 allows the display part 14 to display a mark or blink the mark indicating that the housing 10 has a predetermined temperature or higher. Alternatively, in a case where the FPD1 includes a sound output section, the sound output section may provide notification that the housing 10 has a predetermined temperature or higher. Alternatively, the controller 11 may notify the console 3 that the temperature of the housing 10 is equal to or higher than the predetermined temperature via the communication section 19. Next, the controller 11 may cause the display part or the sound output section of the console 3 to provide notification that the housing 10 has a predetermined temperature or higher.

In step S7, the controller 11 determines whether the imaging has been completed (step S7).

For example, when an imaging end signal is received from the console 3, the controller 11 determines that the imaging has ended.

When it is determined that the imaging is not finished (step S7; NO), the controller 11 returns the process to step S4.

If the controller 11 determines that the imaging has been completed (step S7; YES), the controller 11 determines whether there has been a request to maintain the second power consumption mode (step S8).

The controller 11 determines, for example, whether a request to maintain the second power consumption mode has been received from the console 3.

Here, a predetermined shift time is required for the shift from the second power consumption mode to the standby state and the shift from the standby state to the second power consumption mode. Therefore, maintenance of the second power consumption mode may be required from the console 3.

If the controller 11 determines that there has been a request to maintain the second power consumption mode from the console 3 (step S8; YES), the controller 11 determines whether or not the FPD1 is in contact with the heat suppressing section 4 (step S9).

If the controller 11 determines that the FPD1 is in contact with the heat suppressing section 4 (YES in step S9), the controller 11 maintains the driving of the readout circuit 16 in the second power consumption mode (step S10) and returns the process to step S8.

On the other hand, if the controller 11 determines that there is no request to maintain the second power consumption mode from the console 3 (step S8; NO) or determines that the FPD1 is not in contact with the heat suppressing section 4 (step S9; NO), the controller 11 causes the readout circuit 16 to shift to the standby state (step S14). Then, the controller 11 ends the readout circuit control processing A.

On the other hand, if it is determined in step S1 that the FPD1 is not in contact with the heat suppressing section 4 (NO in step S1), the controller 11 prohibits imaging in the second power consumption mode. Further, the controller 11 enables imaging in the first power consumption mode (step S11), and shifts the processing to step S12.

That is, the controller 11 prohibits driving of the readout circuit 16 in the second power consumption mode, and enables driving of the readout circuit 16 in the first power consumption mode.

In step S12, the controller 11 drives the readout circuit 16 in the first power consumption mode (step S12).

Next, the controller 11 determines whether the imaging is finished (step S13).

When it is determined that the imaging is not finished (step S13; NO), the controller 11 returns the process to step S12.

In a case where it is determined that the imaging is finished (step S13; YES), the controller 11 causes the readout circuit 16 to shift to the standby state (step S14), and finishes the readout circuit control processing A.

In the case where no FPD1 is in contact with the heat suppressing section 4 in the above-described readout circuit control processing A, the driving of the readout circuit 16 in the second power consumption mode is prohibited. Therefore, since the readout circuit 16 can be driven in the second power consumption mode only when the temperature rise of the housing 10 can be suppressed by the heat suppressing section 4, the second moving image imaging mode can be used safely.

Second Embodiment

Next, a second embodiment of the present invention will be described.

The configuration of the FPD1 in the second embodiment is the same as that described in the first embodiment, and the description is therefore incorporated herein. Hereinafter, the operation of the FPD1 in the second embodiment will be described.

In the second embodiment, when the power supply of the FPD1 is turned on, the controller 11 causes each unit to shift to a standby state. Upon reception of the information on the imaging conditions including the imaging mode from the console 3 and the imaging start instruction signal by the communication section 19, the controller 11 executes the readout circuit control processing B.

Figure 4:
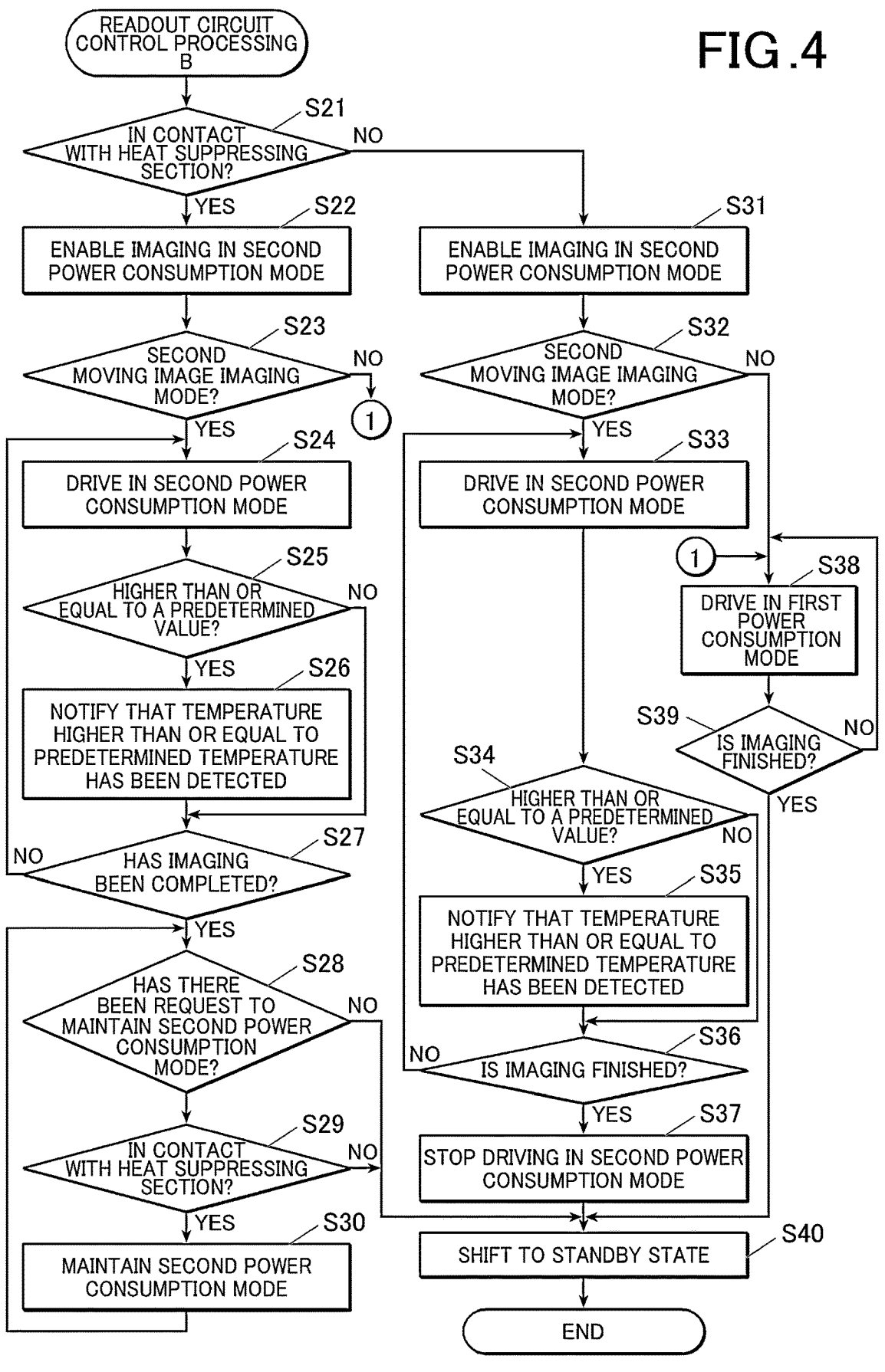
FIG. 4 is a flowchart illustrating a flow of readout circuit control processing B executed by the controller of FIG. 2.

FIG. 4 is a flowchart illustrating a flow of readout circuit control processing B executed by the controller 11. The readout circuit control processing B is executed by the controller 11 in cooperation with the program stored in the storage section 12.

In the readout circuit control processing B, first, the controller 11 determines whether or not the FPD1 is in contact with the heat suppressing section 4 (step S21).

The processing in step S21 is the same as that described in step S1, and thus the description is incorporated herein.

If it is determined that the FPD1 is in contact with the heat suppressing section 4 (YES in step S21), the controller 11 enables imaging in the second power consumption mode (step S22).

That is, the controller 11 enables driving of the readout circuit 16 in the second power consumption mode.

Next, the controller 11 determines whether or not the imaging mode is the second moving image imaging mode (step S23).

The controller 11 determines whether or not the imaging mode is the second moving image imaging mode based on the information of the imaging mode transmitted from the console 3.

If the controller 11 determines that the imaging mode is not the second moving image imaging mode (step S23; NO), the controller 11 moves the process to step S38.

That is, when it is determined that the imaging mode is the first moving image imaging mode or the still-image imaging mode, the controller 11 shifts the processing to step S38.

If it is determined that the image imaging mode is the second moving image imaging mode (YES in step S23), the controller 11 drives the readout circuit 16 in the second power consumption mode (step S24).

Next, the controller 11 refers to the temperature detecting section 21 and determines whether the temperature of the housing 10 at the FPD1 is higher than or equal to a predetermined value (step S25).

If the controller 11 determines that the temperature of the housing 10 at the FPD1 is not higher than or equal to the predetermined temperature (step S25; NO), the controller 11 moves the process to step S27.

If the controller 11 determines that the temperature of the housing 10 at the FPD1 is higher than or equal to the predetermined temperature (YES in step S25), the controller 11 provides notification (warning) that the temperature of the housing 10 at the FPD1 has become higher than or equal to the predetermined temperature (step S26). Next, the controller 11 allows the process to proceed to step S27.

The processing in step S26 is the same as that described in step S6, and thus the description thereof is incorporated herein.

In step S27, the controller 11 determines whether the imaging has been completed (step S27).

For example, when an imaging end signal is received from the console 3, the controller 11 determines that the imaging has ended.

When determining that the imaging has not been completed (step S27; NO), the controller 11 returns the processing to step S24.

If the controller 11 determines that the imaging has been completed (YES in step S27), the controller 11 determines whether a request to maintain the second power consumption mode has been received from the console 3 (step S28).

If the controller 11 determines that there has been a request to maintain the second power consumption mode from the console 3 (step S28; YES), the controller 11 determines whether or not the FPD1 is in contact with the heat suppressing section 4 (step S29).

When it is determined that the FPD1 is in contact with the heat suppressing section 4 (step S29; YES), the controller 11 maintains the driving of the readout circuit 16 in the second power consumption mode (step S30), and returns the process to step S28.

On the other hand, if the controller 11 determines that there is no request to maintain the second power consumption mode from the console 3 (step S28; NO) or determines that the FPD1 is not in contact with the heat suppressing section 4 (step S29; NO), the controller 11 causes the readout circuit 16 to shift to the standby state (step S40). Then, the controller 11 ends the readout circuit control processing B.

On the other hand, when determining in step S21 that the FPD1 is not in contact with the heat suppressing section 4 (step S21; NO), the controller 11 enables imaging in the second power consumption mode (step S31).

That is, the controller 11 enables driving of the readout circuit 16 in the second power consumption mode.

Next, the controller 11 determines whether or not the imaging mode is the second moving image imaging mode (step S32).

If the controller 11 determines that the imaging mode is not the second moving image imaging mode (step S32; NO), the controller 11 moves the process to step S38.

That is, when it is determined that the imaging mode is the first moving image imaging mode or the still-image imaging mode, the controller 11 shifts the processing to step S38.

If it is determined that the image imaging mode is the second moving image imaging mode (YES in step S32), the controller 11 drives the readout circuit 16 in the second power consumption mode (step S33).

Next, the controller 11 refers to the temperature detecting section 21 and determines whether the temperature of the housing 10 at the FPD1 is higher than or equal to a predetermined value (step S34).

If the controller 11 determines that the temperature of the housing 10 at the FPD1 is not higher than or equal to the predetermined temperature (step S34; NO), the controller 11 moves the process to step S36.

If the controller 11 determines that the temperature of the housing 10 on the FPD1 is higher than or equal to the predetermined temperature (YES in step S34), the controller 11 provides notification (warning) that a predetermined temperature or higher has been detected in the housing 10 on the FPD1 (step S35).

The processing in step S35 is the same as that described in step S6, and thus the description thereof is incorporated herein.

Next, the controller 11 allows the process to proceed to step S36.

In step S36, the controller 11 determines whether the imaging has been completed (step S36).

When it is determined that the imaging is not finished (step S36; NO), the controller 11 returns the process to step S33.

If the controller 11 determines that the imaging has been completed (YES in step S36), the controller 11 stops driving the readout circuit 16 in the second power consumption mode (step S37). Then, the controller 11 causes the readout circuit 16 to shift to the standby state (step S40), and ends the readout circuit control processing B.

In step S38, the controller 11 drives the readout circuit 16 in the first power consumption mode (step S38).

Next, the controller 11 determines whether the imaging has been completed (step S39).

When it is determined that the imaging is not finished (step S39; NO), the controller 11 returns the process to step S38.

In a case where it is determined that the imaging is finished (step S39; YES), the controller 11 causes the readout circuit 16 to shift to the standby state (step S40), and finishes the readout circuit control processing B.

In the case where no FPD1 is in contact with the heat suppressing section 4 in the above-described readout circuit control processing B, imaging in the second power consumption mode is enabled on the premise that the driving of the readout circuit 16 is stopped without maintaining the second power consumption mode after the completion of imaging. For example, in the case of a medical facility in which the heat suppressing section 4 is attached to an imaging table in a hospital, imaging during doctor's rounds is conceivable as a use case where the FPD1 does not contact the heat suppressing section 4. Since imaging is performed with the power stored in the battery 17 in the round visit imaging, an imageable time is limited in a case where fluoroscopy is performed in the round visit. Therefore, when fluoroscopy is performed in a round visit, the imaging time is shortened, the temperature rise of the housing 10 in the FPD1 is suppressed, and no thermal injury occurs. Therefore, for example, in a medical facility where the heat suppressing section 4 is attached to an imaging table in a hospital, the readout circuit control processing B is executed by the controller 11 in the FPD1 at the time of imaging. Next, the controller 11 performs control so as to enable driving of the readout circuit 16 in the second power consumption mode even without contact with the heat suppressing section 4, and stop driving of the readout circuit 16 in the second power consumption mode after the completion of imaging. Thus, even in a case where the heat suppressing section 4 is not in contact, it is possible to suppress an increase in surface temperature of the housing 10 on the FPD1, and it is possible to perform imaging in the second power consumption mode safely.

As described above, when in contact with the heat suppressing section 4, the controller 11 of the FPD1 enables imaging in the second power consumption mode. When not in contact with the heat suppressing section 4, the controller 11 prohibits imaging in the second power consumption mode, or stops driving of the readout circuit 16 in the second power consumption mode after the end of imaging in the second power consumption mode.

Therefore, an increase in surface temperature of the housing 10 at the FPD1 can be suppressed, so that the second power consumption mode can be used safely.

Further, FPD1 has a first moving image imaging mode and a second moving image imaging mode in which imaging can be performed at the same frame rate. The controller 11 drives the readout circuit 16 in the first power consumption mode in the first moving image imaging mode and drives the readout circuit 16 in the second power consumption mode in the second moving image imaging mode. Therefore, even in the second moving image imaging mode in which imaging is performed in the second power consumption mode with high power consumption, imaging can be performed at the same frame rate as in the first moving image imaging mode.

The first moving image imaging mode is a serial imaging mode, and the second moving image imaging mode is a fluoroscopy mode.

Therefore, imaging can be safely performed at the same frame rate in the serial imaging mode and the fluoroscopy mode.

Furthermore, the FPD1 includes a temperature detecting section 21 that detects the temperature of the housing 10, and when the temperature detecting section 21 detects a temperature equal to or higher than a predetermined temperature, the controller 11 causes the display part 14 or the communication section 19 to notify the detection of the temperature equal to or higher than a predetermined temperature.

Therefore, for example, in a case where heat generation more than expected occurs such as a case where the heat suppressing section 4 does not function, it is possible to notify a user of danger.

Note that the description in the above embodiment is a preferred example of the present invention, and the present invention is not limited to this.

For example, the temperature detecting section 21 may be installed not only in the vicinity of the readout circuit 16 but also in the vicinity of a component (e.g., an FPGA) that generates a large amount of heat other than the readout circuit 16. Thus, it is possible to perform temperature detection in consideration of a temperature increase distribution in each place of the housing 10.

In addition, the threshold value for determining whether or not a temperature equal to or higher than a predetermined temperature is detected by the temperature detecting section 21 may be converted in consideration of the electrothermal properties of the temperature detecting section 21 and the housing 10. In a case where there are a plurality of temperature detecting sections 21, the conversion factor may be switched for each of the temperature detectors. Thus, it is possible to accurately calculate the heat generation of the housing 10 based on the measurement value of each installation place of the temperature detecting section 21.

In addition, for example, the controller 11 of the FPD1 may apply a guard so that the second power consumption mode cannot be used according to the remaining battery level. For example, the controller 11 may prohibit imaging in the second power consumption mode when a certain amount or more of the battery does not remain in imaging in which the battery is limited, such as mobile imaging performed without receiving power supply from an external device by wire.

In addition, when fluoroscopy is not performed at the time of round imaging, the controller 11 of the FPD1 may apply a guard so that the second power consumption mode cannot be used at the time of round imaging.

Further, the controller 11 may stop the driving of the readout circuit 16 when a temperature equal to or higher than a predetermined temperature is detected by the temperature detecting section 21.

In the above description, an example in which a semiconductor nonvolatile memory or the like is used as a computer-readable medium of the program according to the present invention has been disclosed, but the present invention is not limited to this example. As another computer-readable medium, a portable recording medium such as a hard disk or a CD-ROM can be applied. In addition, a carrier wave is also applied as a medium for providing data of the program according to the present invention via a communication line.

Besides, the detailed configurations and detailed operations of the FPD and the heat suppressing section can also be appropriately modified without departing from the spirit and scope of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2023-115101 filed on Jul. 13, 2023 including description, claims, drawings and abstract is incorporated herein by reference.

What is claimed is:

1. A radiation image imaging apparatus comprising:
a radiation detector that detects radiation;
a hardware processor that controls imaging of a radiation image by driving a readout circuit that reads out an image signal from the radiation detector in a first power consumption mode or a second power consumption mode in which power consumption is larger than power consumption in the first power consumption mode; and
a housing that houses the radiation detector and the hardware processor, wherein
the hardware processor
enables imaging in the second power consumption mode in response to the radiation image imaging apparatus being in contact with a heat suppressor that suppresses an increase in a surface temperature of the housing, and
prohibits the imaging in the second power consumption mode or stops driving of the readout circuit in the second power consumption mode after end of the imaging in the second power consumption mode in response to the radiation image imaging apparatus being not in contact with the heat suppressor.

2. The radiation image imaging apparatus according to claim 1, wherein
the radiation image imaging apparatus includes a first moving image imaging mode and a second moving image imaging mode, and moving image imaging is performed at a same frame rate in the first moving image imaging mode and in the second moving image imaging mode, and
the hardware processor drives the readout circuit in the first power consumption mode in the first moving image imaging mode and drives the readout circuit in the second power consumption mode in the second moving image imaging mode.

3. The radiation image imaging apparatus according to claim 2, wherein the first moving image imaging mode is a serial imaging mode, and the second moving image imaging mode is a fluoroscopy mode.

4. The radiation image imaging apparatus according to claim 1, wherein the heat suppressor is at least one of an air cooling mechanism, a water cooling mechanism, a heat storage material, and a heat transfer material.

5. The radiation image imaging apparatus according to claim 1, further comprising:

a temperature detector that detects a temperature of the housing; and a notifier that notifies detection of a temperature that is a predetermined temperature or higher in response to the temperature being detected by the temperature detector.

\* \* \* \* \*